US010837033B2

(12) United States Patent
Luedtke et al.

(10) Patent No.: US 10,837,033 B2
(45) Date of Patent: Nov. 17, 2020

(54) METHOD FOR MATERIAL USE OF ORGANIC SUBSTRATE

(71) Applicant: VERBIO VEREINIGTE BIOENERGIE AG, Leipzig (DE)

(72) Inventors: Oliver Luedtke, Markkleeberg (DE); Michael Schlimbach, Halle (DE); Enrico Fichter, Leipzig (DE)

(73) Assignee: VERBIO VEREINIGTE BIOENERGIE AG, Leipzig (DE)

( * ) Notice: Subject to any disclaimer, the term of this patent is extended or adjusted under 35 U.S.C. 154(b) by 0 days.

(21) Appl. No.: 15/736,205

(22) PCT Filed: Jun. 6, 2016

(86) PCT No.: PCT/EP2016/062736
§ 371 (c)(1),
(2) Date: Dec. 13, 2017

(87) PCT Pub. No.: WO2016/202616
PCT Pub. Date: Dec. 22, 2016

(65) Prior Publication Data
US 2018/0155746 A1    Jun. 7, 2018

(30) Foreign Application Priority Data
Jun. 15, 2015 (DE) .................. 10 2015 210 871

(51) Int. Cl.
| | |
|---|---|
| *C12P 7/40* | (2006.01) |
| *C12P 5/02* | (2006.01) |
| *C12N 1/14* | (2006.01) |
| *C12N 1/20* | (2006.01) |
| *C12P 7/52* | (2006.01) |
| *C12P 7/22* | (2006.01) |
| *C12P 17/10* | (2006.01) |

(52) U.S. Cl.
CPC ............... *C12P 7/52* (2013.01); *C12P 5/02* (2013.01); *C12P 5/023* (2013.01); *C12P 7/22* (2013.01); *C12P 7/40* (2013.01); *C12P 17/10* (2013.01); *Y02E 50/30* (2013.01)

(58) Field of Classification Search
CPC ...... C12P 5/02; C12P 7/22; C12P 7/40; C12N 1/20; Y02E 50/343
USPC ........................ 435/289.1, 42, 170
See application file for complete search history.

(56) References Cited

U.S. PATENT DOCUMENTS

| | | | |
|---|---|---|---|
| 5,874,263 A | 2/1999 | Holtzapple et al. | |
| 2010/0285548 A1* | 11/2010 | Friedmann | C12P 5/023 435/158 |
| 2013/0137153 A1 | 5/2013 | Elbeshbishy et al. | |
| 2014/0154754 A1* | 6/2014 | Stephens | C12P 3/00 435/128 |
| 2015/0299635 A1 | 10/2015 | Bhasin | |

FOREIGN PATENT DOCUMENTS

| | | |
|---|---|---|
| DE | 19937876 C2 | 11/2002 |
| DE | 102011106772 A1 | 1/2013 |
| EP | 0918876 B1 | 10/2003 |
| EP | 2419516 B1 | 3/2015 |
| WO | 2007014717 A1 | 2/2007 |
| WO | 2014072756 A1 | 5/2014 |

OTHER PUBLICATIONS

WO2007/014717 , 2007, an English translation.*
International Search Report mailed in PCT/EP2016/062736 dated Aug. 8, 2016.
K.N Joblin: "Methods in Gut Microbial Ecology for Ruminants", Ch. 2.3, H.P.S. Makkar and C.S. McSweeney (eds.), 47-53. 2005 IAEA. Printed in the Netherlands.

* cited by examiner

*Primary Examiner* — Robert B Mondesi
*Assistant Examiner* — Mohammad Y Meah
(74) *Attorney, Agent, or Firm* — Fox Rothschild LLP

(57) ABSTRACT

The invention relates to a method for obtaining at least one organic target product and biogas. The method is characterised in that a) organic substrate is introduced into an anaerobic fermentation process; b) in this anaerobic fermentation process a hydrolysis, acidification and methanation are performed using a mixed culture of bacteria and archaea without spatial separation; c) partial suppression of the anaerobic fermentation is realised, with the result that a part of the organic substrate is not completely decomposed to biogas or methane; d) at least one target product is enriched as an organic metabolite of at least one microorganism in the fermentation process by deliberate incomplete composition of the organic substrate; e) the biogas formed in the anaerobic fermentation process is recovered for further use; and f) at least one organic target product is obtained from the anaerobic fermentation process for further use.

8 Claims, 4 Drawing Sheets

METHOD FOR MATERIAL USE OF ORGANIC SUBSTRATE

CROSS REFERENCE TO RELATED APPLICATIONS

This U.S. Application is a National Stage Entry of PCT/EP2016/062736 filed on Jun. 6, 2016, which claims priority to German Application No. 10 2015 210 871.6 filed Jun. 15, 2015, entitled "METHOD FOR SIMULTANEOUS PRODUCTION OF BIOGAS AND AN ORGANIC COMPOUND" the entireties of which are hereby incorporated herein by reference.

BACKGROUND OF THE INVENTION

Technical Area

The invention relates to a method for material use of organic substrate by an anaerobic decomposition process, wherein the organic substrate is decomposed to yield at least one organic target product and biogas.

DESCRIPTION OF THE RELATED ART

The decomposition of organic substrate by microbial anaerobic processes, also called fermentations, is known. Such fermentations are typically conducted with the objective of obtaining a valuable product from a relatively inexpensive substrate. The substrate used is an organic substance or a mixture of various organic substances. Certain microorganisms or groups of microorganisms are suitable for the fermentation process depending on the substrate and the desired product. In order for a fermentation to be carried out successfully, besides supplying the substrate, it must also be ensured that nutrients are supplied and that favourable process parameters such as temperature and pressure are maintained.

The formation of biogas or biomethane from organic substrate is an example of a microbial anaerobic process that is has been put to technical use. In recent years, biogas production has grown increasingly important. Whereas initially the main focus of interest in the treatment of wastewater sludge was the reduction of sludge with biogas formation as a side effect, in recent years the focus has shifted to the recovery of biogas from agricultural cultivated biomass such as whole crop silage, to some extent also combined with the fermentation of manure or other excrement associated with animal husbandry. In order to achieve high profitability, such a biogas process must return the highest possible biogas yield relative to the organic substrate used. A number to technical suggestions have been put forward with this objective in mind. The related art for achieving high biogas yields are a moderate, uniform substrate load and a sufficient supply of macro- and micronutrients, as well as ensuring the residence time of the substrate in the fermentation process is as long as possible. In this context, with regard to the cost effectiveness of a plant, a compromise must be struck between high space requirement and long residence time and the associated high biogas yield. Usually, the compromise consists in increasing the plant output to the point as which process quality falls measurably, or the process becomes less stable. The evaluation of process quality and/or process stability is carried out on the basis of biogas yield or on the basis of an analysis of the fermenter content for the presence of volatile organic acids (VOA). These VOAs (for example acetic acid, propionic acid, butyric acid and other carboxylic acids) are intermediate products of the anaerobic decomposition of the substrate. Higher concentrations of these relative to methanogenesis in the fermenter content indicate incomplete decomposition of the substrate. Consequently, according to current teaching in biogas production efforts are devoted to achieving a low concentration of VOAs. The concentration of VOAs may be determined quantitatively for example by chromatographic analyses, or semi-quantitatively as a cumulative parameter (VOA value or VOA/TAC value) using titration procedures.

Concepts for increasing the efficiency of biogas plants with multistage processes also exist. Plants with spatial separation into primary fermenting and secondary fermenting, which in turn may be organised in multiple stages are known to the person skilled in the art and represent standard practice. In some cases, the secondary fermentation is also used at the same time as a storage site for fermentation residue. In this context, the substrate is typically only fed to the primary fermentation. This ensures a minimum residence time of the fresh substrate.

The individual stages are not substantially different from each other in terms of process conditions and their microbiological composition. All decomposition processes take place in parallel.

Such a process is described for example in EP2419516B1. With this method, in the first stage fermentation of the solid-containing substrate takes place with little accumulation VOAs up to a maximum of 4 g/l, preferably up to 2 g/l. In the second stage, the partially liquefied and partially converted substrate is fermented to completion. The aim of dividing the process into two stages and different blends in the two stages is to improve the yield for the overall process. The purpose of maintaining a low VOA content in the first stage is to prevent the formation of methane from being inhibited and is achieved by returning discharge from the second stage.

A spatial separation of the microbiological decomposition processes in a biogas plant with the objective of increasing plant efficiency is also known to the person skilled in the art. Processes of such kind are suggested in DE19937876C2 and DE102011106772A1 for example.

DE19937876C2 discloses a two-stage method which consists of a controlled hydrolysis stage and a spatially separate methanogenesis stage. In the hydrolysis stage, acid formation is promoted and at the same time methanogenesis is suppressed by selective adjustment of the pH value and the redox potential. In the second stage, the process conditions are adjusted in a range that is favourable for the methanogenic microorganisms. The drawback of this process is that during the hydrolysis the pH and redox are regulated by the blowing in of gases, particularly air, since the introduction of oxygen necessarily leads to a partially aerobic decomposition and therewith a reduction of the yield and problems with the further use of the gas.

DE102011106772A1 teaches a two-stage method for generating methane gas from an organic residue containing solids and liquid which consists of hydrolysis and methanogenesis. It is suggested to carry out the hydrolysis in such manner that no methane is formed in this stage, so that solids without methanogenesis potential can be can be separated therefrom. The organic acids contained in the liquid after the solid separation are completely converted into methane gas in the second stage.

Extraction of the organic acids formed in hydrolysis is also known. A process for microbial decomposition of organic substrate in order to recover reusable materials and nutrients is suggested in WO2014072756A1 for example. Its essential feature is microbial hydrolysis and acidification of the substrate to obtain a permeate containing organic acids. Hydrolysis and acidification of the substrate is favoured by adjusting the pH, the redox value, or also the temperature and very short residence time. The permeate containing organic acids is usable in other processes.

A process for obtaining organic acids or salts of organic acids from biomass by anaerobic fermentation is also disclosed in EP0918876B1. It is shown the a pH lower than 5.8 effectively inhibits methanogenesis. Moreover, methanogenesis may be suppressed by metered addition of inhibitors. The gas that forms during anaerobic decomposition to acids consists of carbon dioxide, hydrogen and possibly also methane. It is stated that for a high yield of acids as little gas as possible must be formed.

The currently known methods for fermenting organic substrate are either designed to produce biogas or biomethane or they concentrate on producing organic acids. Whereas organic acids are considered to lower yield in the production of biogas and biomethane and the decomposition thereof is deliberately encouraged, their further decomposition to biogas and biomethane by hydrolysis in the production of recyclable materials is undesirable, and is specifically suppressed.

Concepts do exist for combining a separate hydrolysis and downstream methane fermentation. But these concepts are intended solely to increase the efficiency of biogas and biomethane yield. Moreover, the spatial separation of the microbial decomposition stages introduced in these cases create disadvantages in terms of gas formation, since gas is released in the hydrolysis stage as well, which gas also contains significant quantities of hydrogen and methane besides carbon dioxide. Furthermore, particularly with protein-rich substrates hydrogen sulphide is also formed in the hydrolysis and acidification. In all cases, the gas stream from the hydrolysis must undergo a purification step. An economical use of the gas stream obtained from a pure hydrolysis and/or acidification process is difficult.

There are no methods known that result in the production of a target product and biogas or methane at the same time in one reaction chamber without the spatial separation of the various decomposition stages.

Object and Solution

It is therefore the object of the invention to transform organic substrate, in particular organic residues as well, into at least one organic target product and biogas with an efficient, inexpensive anaerobic decomposition process and thus achieve significant added value.

The object is solved with a method for obtaining at least one organic target product and biogas comprising the following steps:
a) Introducing the organic substrate into an anaerobic fermentation process
b) Performing the hydrolysis, acidification and methanation using a mixed culture of bacteria and archaea without spatial separation in this fermentation process
c) Incomplete decomposition of the organic substrate to biogas or methane by partial suppression of the anaerobic fermentation process
d) Enriching at least one target product as an organic metabolite of at least one microorganism in the fermentation medium by deliberate incomplete decomposition of the organic substrate
e) Obtaining the biogas formed in the anaerobic fermentation process for further use
f) Obtaining at least one organic target product from the anaerobic fermentation process for further use.

In order to solve this object, the invention provides a method according to claim 1.

Advantageous further developments are defined in the dependent claims. The wording of all claims is structured to reflect their reference to the content of the description.

In a preferred embodiment, the method according to the invention is designed such that the fraction of hydrogen in the biogas formed in the anaerobic fermentation process is less than 5%, preferably less than 2%, particularly preferably less than 1%.

In a further preferred embodiment, the method according to the invention is designed such that at least two target products are obtained separately from the anaerobic fermentation process.

In a further preferred embodiment, the method according to the invention is designed such that one of the target products contains an organic acid.

In a further preferred embodiment, the method according to the invention is designed such that one of the target products contains an aromatic compound.

In a further preferred embodiment, the method according to the invention is designed such that a substance stream occurring during the recovery of a target product is reintroduced into an anaerobic fermentation process.

In a further preferred embodiment, the method according to the invention is designed such that the enrichment of at least one target product is controlled by the hydraulic residence time of the anaerobic fermentation process.

In a further preferred embodiment, the method according to the invention is designed such that the enrichment of at least one target product is controlled by the substrate feed of the anaerobic fermentation process.

In a further preferred embodiment, the method according to the invention is designed such that the enrichment of at least one target product is controlled by the temperature of the anaerobic fermentation process.

In a further preferred embodiment, the method according to the invention is designed such that the enrichment of at least one target product is controlled by limiting at least one nutrient in the anaerobic fermentation process.

In a further preferred embodiment, the method according to the invention is designed such that the enrichment of at least one target product is controlled by limiting at least one nutrient consisting of the elements boron, iron, potassium, cobalt, copper, magnesium, manganese, molybdenum, sodium, nickel, phosphorus, sulphur, selenium, nitrogen, tungsten or zinc in the anaerobic fermentation process.

In a further preferred embodiment, the method according to the invention is designed such that the enrichment of at least one target product is controlled by the concentration of an inhibitor in the anaerobic fermentation process.

In a further preferred embodiment, the method according to the invention is designed such that the enrichment of at least one target product is controlled by the concentration of the sulphide content in the anaerobic fermentation process.

In a further preferred embodiment, the method according to the invention is designed such that the enrichment of at least one target product is controlled by the concentration of the ammonium content in the anaerobic fermentation process.

In a further preferred embodiment, the method according to the invention is designed such that the enrichment of at least one target product is controlled by the concentration of the ammonium content of at least 4,000 mg/l, preferably at least 5,000 mg/l, particularly preferably at least 6,000 mg/l and most particularly preferably at least 7,000 mg/l in the fermentation medium.

In a further preferred embodiment, the method according to the invention is designed such that at least one target product is obtained by stripping.

In a further preferred embodiment, the method according to the invention is designed such that at least one target product is obtained by at least one thermal separation method, such as distillation for example.

In a further preferred embodiment, the method according to the invention is designed such that at least one target product is obtained by extraction.

In a further preferred embodiment, the method according to the invention is designed such that a target product is obtained following a solid-liquid separation of the fermentation medium.

In a further preferred embodiment, the method according to the invention is designed such that the anaerobic fermentation process is carried out in multiple stages.

In a further preferred embodiment, the method according to the invention is designed such that the anaerobic fermentation process takes place with a pH value higher than 6, preferably higher than 7, more preferably higher than 7.5.

In a further preferred embodiment, the method according to the invention is designed such that the anaerobic fermentation process is conducted at least quasi-continuously.

In a further preferred embodiment, the method according to the invention is designed such that at least one target product is obtained simultaneously with the fermentation.

In a further preferred embodiment, the method according to the invention is designed such that at least one target product is obtained after a first fermentation process.

In a further preferred embodiment, the method according to the invention is designed such that one of the target products contains an organic acid.

In a further preferred embodiment, the method according to the invention is designed such that one of the target products contains an aromatic compound.

In a further preferred embodiment, the method according to the invention is designed such that at least one target product is obtained by stripping.

In a further preferred embodiment, the method according to the invention is designed such that at least one target product is obtained by at least one thermal separation method, such as distillation for example.

In a further preferred embodiment, the method according to the invention is designed such that at least one target product is obtained by extraction.

In a further preferred embodiment, the method according to the invention is designed such that the anaerobic fermentation process is conducted at least quasi-continuously.

In a further preferred embodiment, the method according to the invention is designed such that at least one target product is obtained simultaneously with the fermentation.

In a further preferred embodiment, the method according to the invention is designed such that at least one target product is obtained after a first fermentation process.

In a further preferred embodiment, the method according to the invention is designed such that organic substrate is fermented to form biogas in a one-stage anaerobic process.

The method according to the invention also relates particularly to all combinations of the preferred embodiments described in the preceding text.

Description of the Solution

Organic substrate may be converted into biogas by controlled microbial decomposition. The microbial decomposition takes place essentially in three stages. These are hydrolysis, acidification and methanogenesis. While in the first two decomposition stages the decomposition of the organic substrate is catalysed by a multiplicity of obligate and facultative anaerobic bacteria, obligate anaerobic archaea are responsible for methanogenesis. In the complete decomposition of the organic substrate, essentially consisting of the elements C, H, O, N, S and P, carbon dioxide, methane and water as well as ammonia, hydrogen sulphide and inorganic phosphate are formed as end products. The end products escape as gases or remain as ions dissolved in the aqueous medium depending on the process conditions.

This decomposition process proceeds substantially in a cascade reaction. Thus, the substances form from macromolecules during the hydrolysis, mostly long-chain organic acids, function as starting materials for the acidification. During the acidification, the metabolites from the hydrolysis are broken down further. The acidification is itself also structured as a cascade reaction to a degree, since larger or longer-chain organic acid are progressively reduced to lower-molecular acids. Finally, the acetic acid formed serves as the starting material in the acetoclastic methanogenesis. During this decomposition cascade, particularly during the acidification, carbon dioxide and hydrogen are formed as byproducts. The hydrogen formed is converted with a portion of the carbon dioxide to form methane by hydrogenotrophic methanogenesis.

The very close interrelationship between the various stages of decomposition in terms of both material and energy has been researched extensively. It is known that hydrolysis and acidification can be separated spatially from methanogenesis. This is not difficult, since different forms of microorganisms with differing optimal growth conditions are involved. Thus, by a series of measures the methanogenesis may be selectively suppressed. A low pH value, higher redox values for example by introducing atmospheric oxygen, higher temperatures, short residence times and high product concentrations from the acidification lead to suppression and therewith impoverishment of the methanogenesis. In addition, chemical compounds are known to the technical community that when added to the hydrolysis and acid formation stages in metered quantities cause selective inhibition of methanogenesis. Examples of such chemical compounds are aromatic compounds such as phenol, halogen compounds, for example bromethanesulphonic acid and salts thereof or also inorganic compounds such as ammonium or chloride.

Particularly the accumulation of VOAs is often described as inhibiting of methanogenesis. Data in the technical literature is also inconclusive because the measurement methods used in a larger range are not consistent. In general, however, VOAs in quantities greater than 4 g/l are considered critical. Ammonia or ammonium represents a byproduct in the acidification of nitrogen-containing organic compounds. Concerning ammonia inhibition, the differences in findings in the technical literature are even wider. General teaching instructs that higher contents least to inhibition of methanogenesis. This applies equally for the hydrogen sulphide formed during the acidification.

The technical community views a spatial separation of the decomposition stages as an option for increasing efficiency, since the optimum process conditions for the microorganisms involved in each case can be established in each of the separate areas. The inadequacies of this concept are evident at least with regard to hydrogen. In spatially separate systems, the hydrogen formed during hydrolysis is not in direct contact with the microorganisms responsible for the methanogenesis and consequently also cannot be converted directly into methane. The hydrogen must therefore be assessed as lost for the purpose of methanogenesis, or it must be brought into contact with the methanogens with considerable technical effort.

Furthermore, the appeal of a spatial separation of hydrolysis and acidification resides in the enrichment of organic acids. The technical community is familiar with various concepts for obtaining organic acids from aqueous fermentation media. However, these concepts have had little economic significance in the past. Organic acids are obtained either by chemical synthesis from fossil-based starting materials or by special fermentations. In the latter case, typically it is not heterogeneous organic substrates but defined media that are used.

The stated objective of the present invention is the cost-effective preparation of organic target products from organic substrate with simultaneous formation of biogas, particularly biomethane. At the same time, a high total yield of the substrate is critically important with regard to cost effectiveness.

Surprisingly, it has been found that in contradiction of the general doctrine, if the anaerobic fermentation is partly suppressed it is possible to carry out significant enrichment of at least one organic target product in a one-stage anaerobic fermentation process, in which the hydrolysis, acidification and methanation are carried out by a mixed culture of bacteria and archaea without spatial separation while keeping the methane fermentation stable. It was also found that with a series of measures, particularly control of nutrient supply, it is possible to partly suppress anaerobic fermentation and thus influence the enrichment of the target product. In addition, in experiments it was found that it is possible to achieve substrate decomposition that is consistently high compared with complete fermentation. This in turn makes it possible to produce valuable target products as well as biogas or methane with inexpensive organic substrate, such as organic residues, in a simple fermentation method.

In an efficient, cost-effective method, the available organic substrate is introduced into an anaerobically driven fermentation process. The organic substrate may be organic residues from upstream processes, organic residues from the food sector, such as food leftovers, renewable raw materials, particularly straw, or any other organic substances.

Of course, mixtures of the aforementioned substances may also serve as organic substrates. It is advantageous for the process if the substrate composition does not include any more substantial variations. The use of wastewater sludge is rather unsuitable.

The fermenter content consists of incompletely decomposed substrate and contains all microorganisms that are necessary for a complete decomposition of the substrate. This means that in this anaerobic fermentation process the hydrolysis, acidification and methanation are carried out by a mixed culture of bacteria and archaea without spatial separation. In this context, "incompletely decomposed" means that an arithmetical fraction of the substrate has not be completely decomposed to form biogas but is enriched as at least one soluble organic metabolite of at least one microorganism in the liquid phase in the fermentation process. This organic metabolite is the desired target product. It is also possible to classify several different metabolites as desired organic target products, which are to be obtained as a mixture or separately. In the following text, the invention will be explained on the basis of obtaining a desired organic target product and biogas. However, these notes are explicitly not limited thereto, but instead are also applicable to the recovery of multiple organic target products in one fermentation process.

The introduced substrate is decomposed during fermentation to yield the desired organic target product and biogas. In this context, the fermentation may consist of one fermenter or a plurality of fermenters interconnected in any way. The target product is enriched in at least one of the fermenters by partially suppressing the anaerobic fermentation by suitable measures. The biogas formed is extracted from the fermentation for further use. Discharge is also drawn off from the fermentation, so that the fill level of the fermentation systems is maintained in the desired range. The discharge contains the organic target product. In this way, it is also possible to enrich multiple target products in the discharge.

The nutrients necessary for incomplete decomposition are added to the fermentation either with the organic substrate or by the addition of suitable products in metered quantities. These are particularly boron, iron, potassium, cobalt, copper, magnesium, manganese, molybdenum, sodium, nickel, phosphorus, sulphur, selenium, nitrogen, tungsten and zinc. Different potentials for enriching certain target products exist depending on the substrate used. The enrichment of the desired target product and/or partial suppression of anaerobic fermentation may be influenced substantially by the concentration of at least one nutrient. By controlling the metered quantity of at least one relevant nutrient, the concentration of a nutrient may be reduced or increased deliberately to encourage the formation of a target products or suppress the anaerobic decomposition of the enriched target product by limiting and/or inhibiting it. The formation of a target product may also be encouraged or its decomposition prevented by adding metered quantities of an inhibitor.

The introduction of substrate is controlled in such manner that the desired enrichment of the target product is maintained. The introduction of the substrate is also carried out in such manner that a pH in the fermenter content does not fall below a value of 6, preferably 7, more preferably 7.5. In this way, it is ensure that the hydrogen content in the gas is less than 5%, preferably less than 2%, particularly preferably less than 1%.

The fermentation process is carried out by suitable measures in a favourable temperature range. Fermentation processes are usually operated in a mesophilic or thermophilic range. By varying the temperature, it is possible to influence the methane fermentation and therewith the formation of the target product as well. For example a temperature increase of a few degrees may result in more intense enrichment of the target product.

The principle of the invention is evident from the results of experiments on continuous fermentation for the enrichment of target products, particularly propionic acid, and the formation of methane. Essential results of this experiment are shown in FIG. 1. FIG. 1 shows the weekly averages of the propionic acid content in the fermentation medium and of the specific methane yields. The latter are the specific methane yields on the basis of the biogas formed plus the gas potential contained in the target products.

At the start of the experiment, the organic substrate introduced was completely decomposed to form biogas or methane in a mesophilic anaerobic fermentation process. On average, the specific methane yield is approximately 0.33 $m^3/kg$. Thereafter, the content of the nutrients in the fermentation medium was lowered in controlled manner by reducing the metered quantity of nutrient solution added in order to increase the concentration of the target products in the fermentation medium by limitations in the microbial decomposition process. This results in a partial suppression of the anaerobic fermentation and it was possible, for example, to enrich propionic acid to a concentration of 12,000 g/m$^3$ in the fermentation medium. At the same time, the gas yield and the methane yield could be reduced by means of this incomplete decomposition of the substrate. The specific methane yield was reduced to about 0.25 m$^3$/kg. However, if the methane potential of the target products is considered together with the measured, specific methane yield, the result is a methane yield comparable to that at the start of the experiment with complete substrate decomposition. Even during enrichment of the target products and in the stationary range at the end of the experiment, this calculated specific methane yield is in the order of approximately 0.33 m$^3$/kg. Accordingly, the enrichment of target products in the fermentation medium does not take place to the detriment of the substrate exploitation. Moreover, it was discovered in the experiment that the fermentation gas consisted solely of the components methane, carbon dioxide and hydrogen sulphide within the limits of measurement accuracy for the entire duration of the experiment. More abundant formation of hydrogen, such as usually occurs with selective formation of acids in a hydrolysis stage and/or acidogenesis, was not reflected in the measurements.

The target product contained in the discharge may be recovered from the discharge and purified with a series of processes. The suitability thereof may vary according to the nature of the primary target product. Possible processes are distillation, extraction, solid-liquid separation, crystallisation, membrane separation and stripping. For the person skilled in the art, it is also self-evident to apply these processes in any combination. The recovery of the target product from the discharge usually takes place downstream of the fermentation process. However, with membrane separation or stripping for example, it is equally possible to combine recovery of the target products with the fermentation process. Depending on requirements, the target product may be recovered as a pure substance, a solution or suspension, or generally as a mixture of substances.

The residues that are generated in the process, such as fermentation residue or process water and process streams with unwanted contents may be transported away, or at least a fraction thereof may be returned to the process. Besides increasing the yield, this may also be used to influence the formation of the target product. The residence time and/or the concentration of relevant content substances in the fermentation process may also be influenced in targeted manner by the use within the process of process streams, particularly process water. This may be used to influence the enrichment of the target product.

In the following text, the invention will be described in detail with reference to several design examples. Of course, it is possible to combine at least parts of the design examples with each other. This is particularly true for recovery involving multiple target products with regard to the method management of the process streams.

DETAILED DESCRIPTION OF PREFERRED EMBODIMENTS

Design examples of the invention are represented in the figures, and will be described in greater detail hereafter.

Design Example 1

Figure 1:
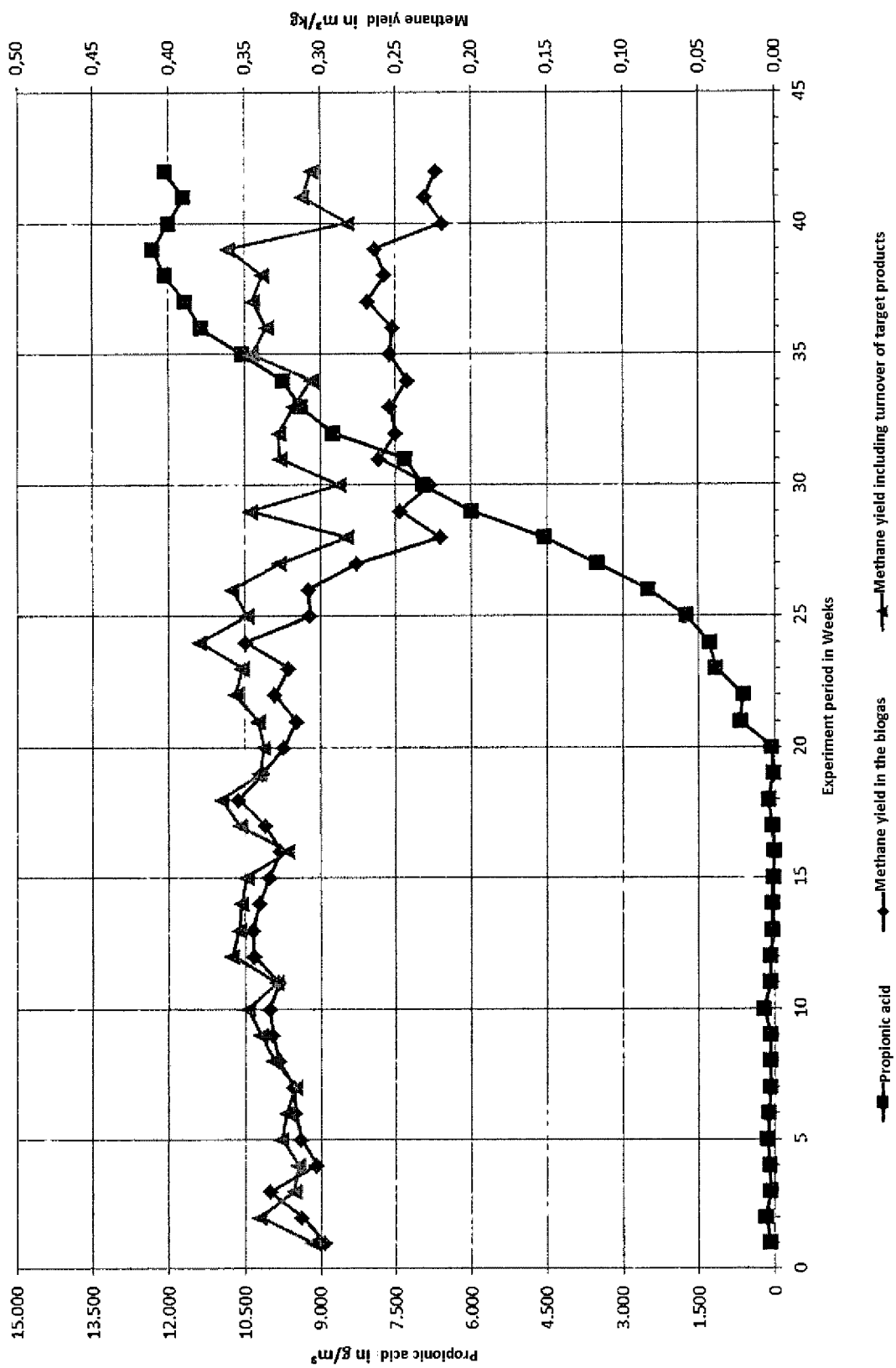
FIG. 1 shows data from a fermentation for the enrichment of propionic acid and formation of methane.
Figure 2:
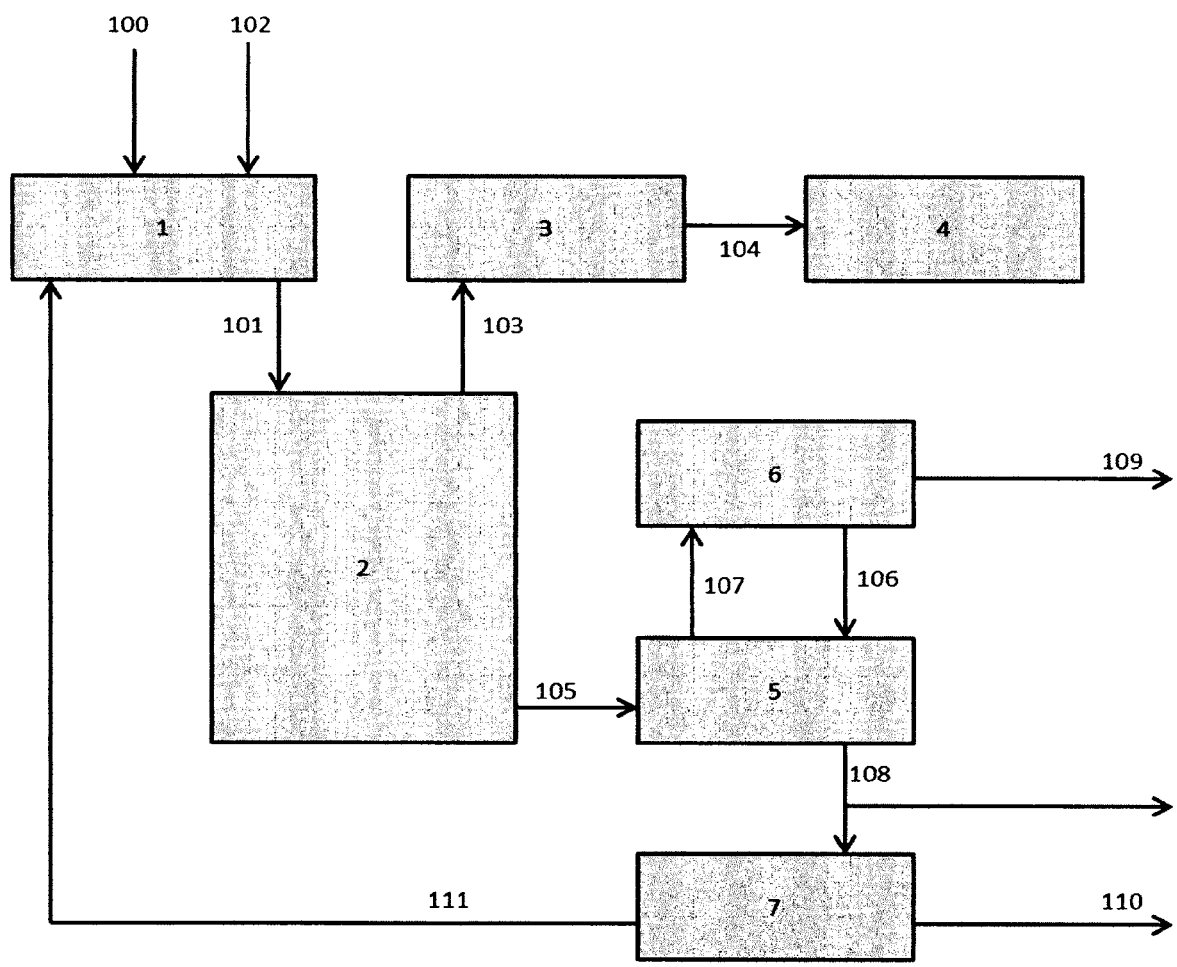
FIG. 2 shows a flowchart of a possible first embodiment according to the invention.

One possible technical design of the method will be illustrated in the following text based on the example of obtaining propionic acid as the target product and biogas. Propionic acid can be formed via microbial decomposition paths from a wide variety of starting materials. For example, decomposition paths from glycerin, amino acids, glucose and other sugars such as pentoses and also from organic acids to propionic acid are known. Of course, other target products such as organic acids and microbiological metabolites or mixtures thereof may also be obtained according to the same principle. Essential features of this design example are also shown in FIG. 2.

Organic residues from the catering and luxury food industry such as meal leftovers and edible remains from breweries or other fermentation methods may be used as organic substrate. The use of these organic residues is financially attractive. The contents may vary depending on the origin of the residue residues. They are characterised by a high proportion of organic residues or nitrogen-free extracts (NFE) and a higher proportion of proteins compares with renewable raw materials.

The bandwidths of dry substance composition are shown in the following table:

| Component | Content |
| --- | --- |
| Raw ash | 5% ... 15% |
| Raw fibre | 3% ... 13% |
| Raw protein | 20% ... 40% |
| Raw fat | 5% ... 20% |
| Organic residue | 30% ... 60% |

In a first process step (1), the organic residues (100) are homogenised and optionally heat treated to create a pumpable, solid-containing organic substrate (101). In this context, process water may be recirculated to set a favourable dry substance content. Substrate (101) has an organic dry substance content of 10% to 25%.

Pumpable substrate (101) is introduced into a continuous anaerobic fermentation process (2). The average burden of fermentation (2) with organic substance is set in a range from 2 to 6 kg/mad. The average residence time is set in a range from 20 to 60 days.

Besides the substrate, nutrients are introduced to the fermentation process at regular intervals. In this way, the microbiology contained in the fermenter may be influenced in targeted manner. By maintaining low contents of copper, selenium and cobalt, the anaerobic fermentation is partially suppressed, as a direct consequence of which the propionic acid content in the fermenter is enriched. Sulphide precipitation in the fermentation process may help to lower the concentrations of these substances. The precipitated compounds are then not available or only available to a very limited degree as nutrients for the microorganisms. The copper, selenium and cobalt contents are reduced to the point at which the accumulation of propionic acid reaches a range from 5,000 to 15,000 mg/l in the fermenter content.

In order to maintain favourable environment conditions, in particular a suitable pH value, the direct or indirect introduction of buffer substances into the fermentation process may be advisable. Besides the use of substrates with sufficient buffer capacity, the pH value may also be influenced by recirculating process liquid. In principle, the addition of measured quantities of buffer solutions such as sodium bicarbonate or lye is also possible, but it also entails additional costs. When the system is operated constantly, and an adequate supply of other nutrients is also assured, a consistently high turnover of the substrate with formation of biogas is possible.

The biogas (103) consists of carbon dioxide and methane as well as hydrogen sulphide. The content of these substances, particularly the hydrogen sulphide content varies according the substrate composition and the process conditions. The presence of sulphur-containing amino acids or also sulphates in the substrate used or in other feeds to the fermentation process leads to higher hydrogen sulphide amounts in the fermenter content and in the gas. The content thereof is typically in a range from 0.1% to 2%. The raw biogas (103) formed is transported out of the fermenter and forwarded to a purification step (3). In this purification step (3). the hydrogen sulphide is removed so that the purified biogas (104) can be used to generate energy in a downstream CHP (4).

The discharge (105) enriched with propionic acid in the fermentation process is transported out of the fermenter and forwarded to an extraction step (5). The extraction agent (106) is a liquid that selectively enriches propionic acid and at the same time is poorly soluble or completely insoluble in water. The presence of the solids contained in the discharge may normally be tolerated during the extraction. The extraction consists of a sequence of mixing and demixing processes with the addition of fresh, partially charged or regenerated extraction agent. In this way an extract (107) containing the propionic acid and a depleted discharge (108) is obtained.

The propionic acid (109) is obtained in a thermal separation stage (6), for example distillation. In this context, the extraction agent is separated from the propionic acid.

While the propionic acid (109) is obtained as a recyclable substance for the chemical industry, for example, the extraction agent (106) may be recirculated in the process again. Losses of the extraction agent must be replenished in the process.

The quality of the propionic acid obtained, depends on the choice of extraction agents and performance of the thermal separation stage. Depending on the requirement of its subsequent use, the propionic acid obtained may also contain water, residues of the extraction agent and other contents such as other organic acids. Acidifying the discharge (105) may be helpful for improving the extraction process.

In this case, bound carbonate is displaced as CO2 and must be transported away.

The depleted discharge (108) contained in the extraction stage may be used in the usual way. Optionally after a solid-liquid separation step (7), the liquid phase (111) obtained thereby may be used for homogenising the substrate. A leftover solid (110) or the depleted discharge (108) may also be sold as fertiliser.

In a further variant, the solid-liquid separation may also be carried out between the fermentation and the extraction. In this case, a solid with propionic acid residues is obtained from the treatment of the discharge, and only the liquid phase produced is forwarded to the extraction, optionally after lowering the pH value. The acid required to adjust the pH of the liquid phase may be significantly less than the acid needed to adjust the pH of the discharge, if substantial buffer capacity is separated with the solid.

Design Example 2

Figure 3:
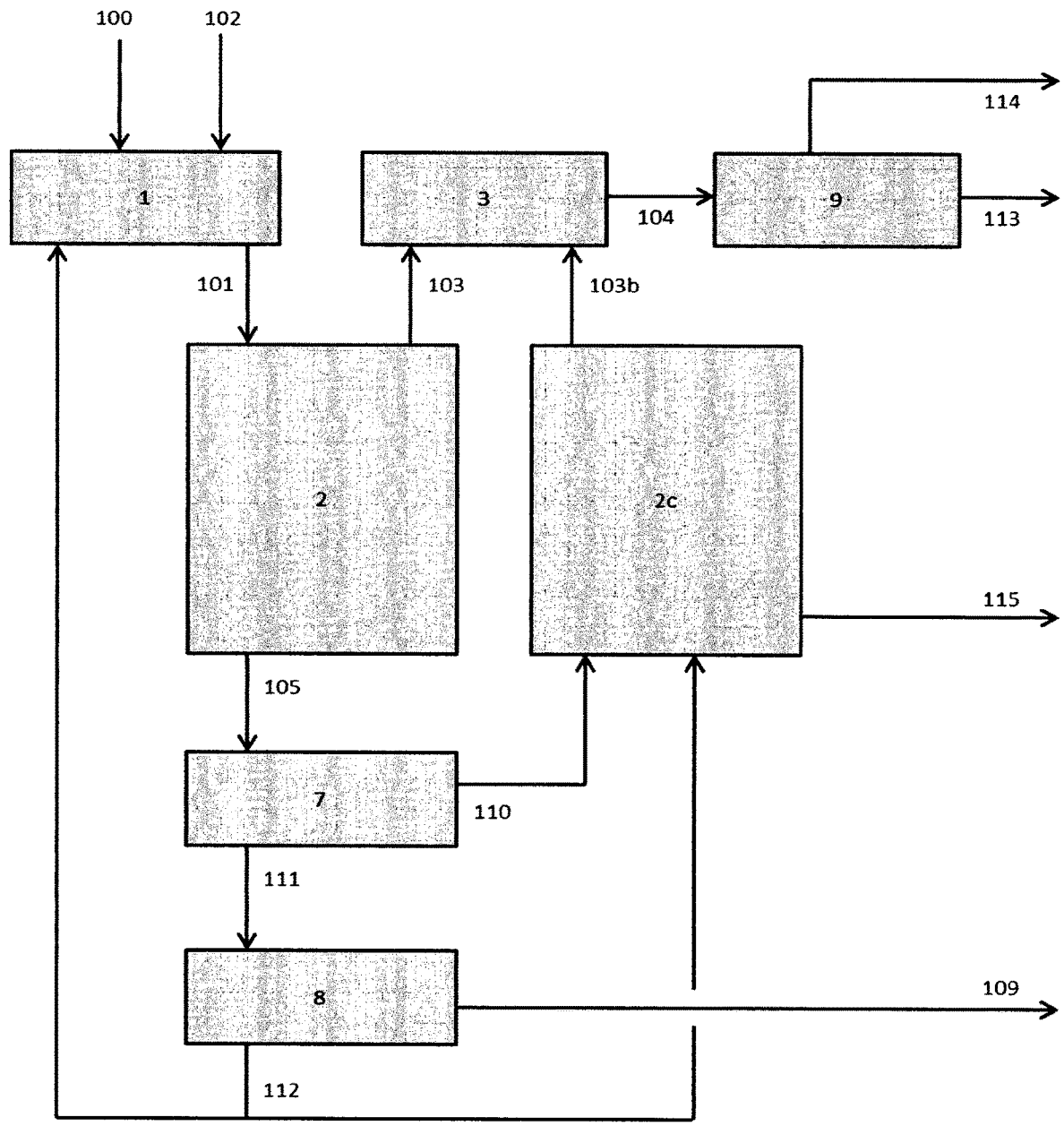
FIG. 3 shows a flowchart of a possible second embodiment according to the invention.

A further possible technical design of the method will be illustrated in the following text based on the example of obtaining aromatic compounds such as cresol and/or skatole and methane. At the same time, these substances represent target products which are produced in the fermentation of particularly protein-rich substrates and which are mostly present in the undissociated state. Essential features of this design example are represented in FIG. 3. The following notes are formulated with only cresol as the target product for exemplary purposes.

Organic residues such as are described in Design example 1 or other organic substrates with relevant protein and/or aromatic compound content are used as organic substrate. Organic substrates particularly with significant contents of the aromatic amino acids phenylalanine, tryptophan or tyrosine, or with contents of other, similar aromatic compounds are interesting for such a process, because possible intermediary metabolites of anaerobic decomposition may be the target products cresol and/or skatole. These two target products can be completely decomposed anaerobically with prolonged residence times and a sufficient supply of nutrients.

In a first process step (1), the organic residues (100) are homogenised and optionally heat treated to create a pumpable organic substrate (101). In this context, process water may be recirculated to set a favourable dry substance content. Substrate (101) has an organic dry substance content of 5% to 30%.

The pumpable substrate (101) is fed to a continuous anaerobic fermentation process (2).

The average charge of the fermentation (2) with organic substance is set in a range from 2 to 8 kg/mad. The average residence time is set in a range from less than 50 days, preferably less than 30 days, particularly preferably less than 20 days.

With a high substrate feed and relatively short residence time, partial suppression of the anaerobic fermentation is achieved. In the fermentation, at first mainly readily decomposable substrate components are completely broken down, while aromatic metabolites, particularly cresol, accumulated in the fermentation medium.

The partial suppression of anaerobic fermentation and subsequent anaerobic decomposition of the target product can be influenced with high ammonium contents as well as low micronutrient contents. The nutrient contents may be maintained in favourable ranges by taking regular measurements of the substrates used and the fermentation content, and adapting the metered quantities added. For example, nutrients (102) may be introduced into the admixture (1). When the system is operated constantly, and an adequate supply of other nutrients is also assured, a consistently high turnover of the substrate with formation of biogas is possible.

The discharge (105) containing cresol is transported away from the fermentation (2) and fed to a solid-liquid separation stage (7). In this context, the fill level and thus also the reaction space in the fermentation stage can be kept as constant as possible and at least in a favourable range. The solid-liquid separation (7) produces a solid (110) and a liquid (111). The liquid contains most of the cresol present in the discharge. The liquid (111) is passed to a stripping process (8). In the stripping (8) stage, the steam volatile cresol is displaced from the liquid with a stripping gas, and is obtained in aqueous phase after condensation. The stripping may also be carried out in combination with other separating operations. Higher temperatures favour the stripping process. The solubility of cresol in water can also be exceeded depending on process conditions, yielding a crystallisation product. From the stripping stage (8), the target product cresol (109) is transported away for further use. The depleted liquid (112) is removed from the stripping stage (8) as the second medium.

One part of the depleted liquid (112) is used to adjust the desired residence time by recirculation to the fermentation stage (2). In this context, the depleted liquid may first be added to the admixture (1) or alternatively it may also be forwarded directly to the fermentation stage (2).

The other part of the depleted liquid is fed to the secondary fermentation (2c) together with the solid (110). In the secondary fermentation, the residual gas potential present in the solid and the depleted liquid is used by continuous anaerobic fermentation.

The raw biogas resulting from the secondary fermentation (103b) is fed to a purification stage (3) together with the raw biogas (103) from the first fermentation stage (2). There, hydrogen sulphide and optionally other components are separated. The purified biogas (104) forwarded to the CO2-removal stage (9). There, the carbon dioxide is separated by pressure swing adsorption for example and transported away (113), while the methane (114) obtained is recovered for further use. After adjustment of its calorific value, the methane may be fed into the natural gas grid, for example and forwarded for material or energy recycling.

The fermentation residue (115) extracted from the secondary fermentation (2c) contains the mineral substances that were introduced with the substrate and/or the nutrients, and can be forwarded for material recycling, as fertiliser for example. In an alternative configuration, a part of the depleted liquid (112) may also be transported away together with the fermentation residue (115) from the secondary fermentation. It is also conceivable to transport it away separately.

In a further variant, it is also possible to extract the target product directly from the fermentation process with a suitable stripping medium. For example, recirculation of biogas through the fermentation medium with precipitation of the target product outside the fermentation is possible.

Design Example 3

Figure 4:
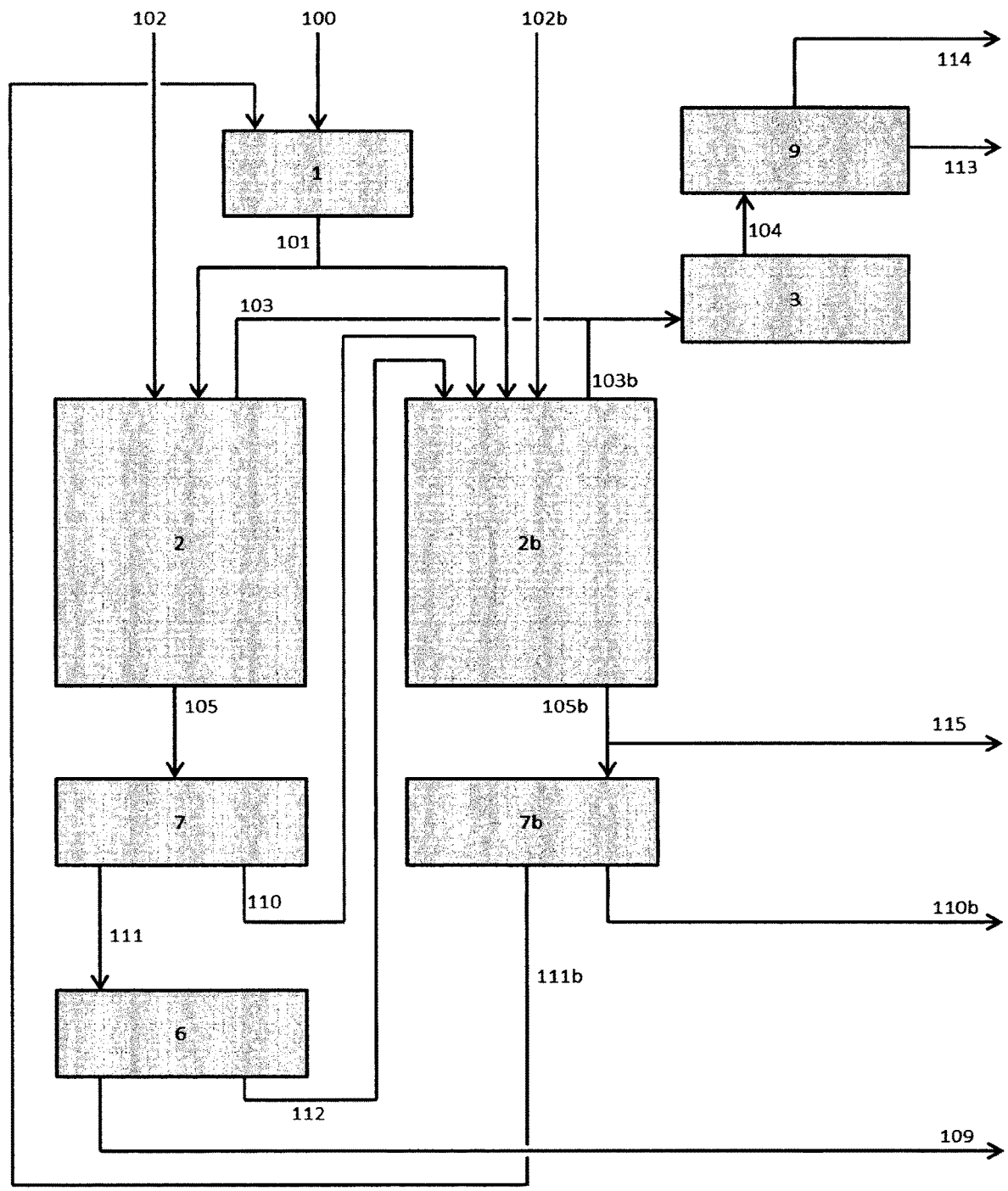
FIG. 4 shows a flowchart of a possible third embodiment according to the invention.

A further possible technical design of the method will be illustrated in the following text based on the example of obtaining isovaleric acid and methane. This method may also be used for recovering other organic acids, particularly short-chain or aromatic carboxylic acids such as isobutyric acid, butyric acid, valeric acid, caproic acid and/or benzoic acid or corresponding mixtures. A characteristic quality for these target product is their accumulation in dissociated form in the fermentation medium. Essential features of this design example are shown in FIG. 4.

Organic residues such as are described in Design example 1 or other organic substrates with relevant organic compound content based on at least C5- and/or C6-structures are used as organic substrate. These may particularly be proteins and/or amino acids as well as carbohydrates such as pentosans. Such compounds may be decomposed anaerobically by means of the metabolite isovaleric acid. Through partial suppression of anaerobic fermentation, it is possible to enrich the isovaleric acid in the fermentation medium. In general, the substrate should contain meaningful quantities of compounds that consist of basic building blocks having at least as many bound C atoms as there are C atoms in the target product.

In a first process step (1), the organic residues (100) are homogenised and optionally heat treated to create a pumpable organic substrate (101). In this context, process water may be recirculated to set a favourable dry substance content. Substrate (101) has an organic dry substance content of 5% to 30%.

A portion of the pumpable substrate (101) is fed to an anaerobic fermentation process (2). Another portion of the substrate is fed to a further fermentation process (2b). It is also possible to carry out the mixing separately for the respective fermentation processes to control the introduction of the residues and/or process waters into the individual fermentation stages.

While in the one fermentation stage (2) the process conditions so are adjusted such that the anaerobic fermentation is partially suppressed and consequently less gas is formed (103) and the isovaleric acid in the fermentation medium is enriched, in the other fermentation stage (2b), the process conditions are chosen such that complete anaerobic decomposition of the substrate is not inhibited, or it is enhanced. The average charge of the fermentation stages (2, 2a) with organic substance is set in a range from 2 to 8 kg/mad. The average residence time is set in a range from 20 to 60 days.

In order to partially suppress the anaerobic fermentation (2) in targeted manner and thus favour the enrichment of isovaleric acid in the fermentation medium, the substance is introduced at a relatively high rate. For the same purpose, a higher fermentation temperature than for the other fermentation stage (2a) is also set, and/or the nutrient supply is reduced and/or the concentration of sulphide and/or ammonium in the fermentation medium is deliberately kept high. Ammonium contents of at least 4,000 mg/l, preferably at least 5,000 mg/l, particularly preferably at least 6,000 mg/l and most particularly preferably at least 7,000 mg/l in the fermentation medium are advantageous.

To ensure that the substrate is used efficiently in anaerobic decomposition, the elements boron, iron, potassium, cobalt, copper, magnesium, manganese, molybdenum, sodium, nickel, phosphorus, sulphur, selenium, nitrogen, tungsten and zinc are important. Depending on the concentration and availability of the respective elements in the added residues and their concentration and availability in the fermentation medium, these must also be introduced additionally. These nutrients (102, 102b) are fed to the respective fermentation stages (2, 2b) separately.

In order to maintain a suitable pH value, it may be advisable to introduce buffer substances directly or indirectly into the fermentation process. Besides the use of substrates with sufficient buffer capacity, the pH value can also be influenced by recirculating process liquid. In principle, the addition of buffer solutions such as sodium bicarbonate or lye in metered quantities is also possible, but it is associated with additional costs. The fermentation is operated with the fermentation medium at a pH value of at least 6, preferably at least 7, more preferably at least 7.5.

The discharge (105) containing isovaleric acid is transported away from the fermentation stage (2) and delivered to a solid-liquid separation stage (7). In this context, the fill level and thus also the reaction space in the fermentation stage can be kept as constant as possible and at least in a favourable range. The solid-liquid separation (7) produces a solid (110) and a liquid (111). The liquid contains most of the isovaleric acid present in the discharge, since it exists mainly in the dissociated form when dissolved.

The liquid (111) is forwarded to a thermal separation stage (6). This thermal separation is for example at least single-stage distillation. The valeric acid is transformed into its undissociated form by lowering the pH value, which in turn improves separation. For efficient separation of isovaleric acid, the miscibility gap with water at higher concentrations is used. This phase may be further separated or fractionated by further purification steps, for example another distillation step. In this way, it is possible to obtain an isovaleric acid phase containing more than 30%, preferably more than 40%, particularly preferably more than 50%, most particularly preferably more than 60%. Specifically in the formation of various organic acids as target products in fermentation stage (2), such a fractionation step may be inserted downstream.

The depleted liquid (112) created in the thermal stage is fed to the other fermentation stage (2b) together with the separated solid (110). Alternatively, the depleted liquid (112) may also be flushed out.

In fermentation stage (2b)m the conditions are set to ensure optimal exploitation of the gas. In this way, not only is the introduced substrate fermented anaerobically to yield biogas, but the residual gas potential possibly present in the solid (110) and the depleted liquid (112) is also used.

The discharge (105b) transported away from fermentation stage (2b) is either at least partially flushed out directly as fermentation residue (115) and forwarded for example for material recycling purposes and/or at least partly introduced to a solid-liquid separation stage (7b) to generate liquid (111b) for mixing the residues or to generate other usage paths. The solid (110b) produced thereby is transported away by suitable means and forwarded for material and/or energy recycling purposes.

The raw biogas formed in fermentations (2, 2b) consists essentially of each of the components methane, carbon dioxide and hydrogen sulphide, and depending on the temperature and pressure, steam as well. Raw biogas (103) also escapes during fermentation (2) to obtain isovaleric acid as the target product, but does not contain significant quantities of hydrogen. The hydrogen content is typically less than 1%.

The raw biogas obtained from fermentations (103, 103b) is forwarded together for purification (3). There, hydrogen sulphide and any other components are separated. The purified biogas (104) is forwarded to the CO2-removal stage (9). There, the carbon dioxide is separated by pressure swing adsorption for example and transported away (113), while the methane (114) obtained is recovered for further use. After adjustment of its calorific value, the methane may be fed into the natural gas grid, for example and forwarded for material or energy recycling.

LIST OF REFERENCE SIGNS

100 Residues
101 Substrate
102 Nutrients
102b Nutrients
103 Raw biogas
103b Raw biogas
104 Biogas
105 Discharge
105b Discharge
106 Extraction agent
107 Extract
108 Depleted discharge
109 Target product
110 Solid
110b Solid
111 Liquid
111b Liquid
112 Depleted liquid
113 CO2
114 Methane
115 Fermentation residue
1 Admixture
2 Fermentation
2b Fermentation
2c Secondary fermentation
3 purification
4 CHP
5 Extraction
6 Thermal separation
7 Solid-liquid separation
7b Solid-liquid separation
8 Stripping
9 CO2 removal

The invention claimed is:
1. A method for obtaining at least one organic target product and biogas, wherein
   a) a heterogeneous organic substrate containing at least the elements C, H, O, N, S and P, is introduced into an anaerobic fermentation process;
   b) in this anaerobic fermentation process a hydrolysis, an acidification and a methanation are performed using a mixed culture of bacteria and archaea without spatial separation;
   c) at least one target product selected from the group consisting of aromatic compounds, isovaleric acid, propionic acid and combinations thereof is enriched as an organic metabolite of at least one microorganism by controlling the hydraulic retention time of the anaerobic fermentation process to less than 50 days, and the ammonia concentration in the anaerobic fermentation process to at least 4,000 mg/L and the pH value of the fermentation process to higher than 6;
   d) the biogas formed in the anaerobic fermentation process is recovered for further use; and
   e) at least one of the organic target products obtained from the anaerobic fermentation process is for further use.

2. The method of claim 1, wherein a fraction of hydrogen in the biogas formed in the anaerobic fermentation process is less than 5%.

3. The method of claim 1, wherein at least two of the target products are obtained separately from the anaerobic fermentation process.

4. The method of claim 1, wherein a substance stream occurring during the recovery of the target product is reintroduced into the anaerobic fermentation process.

5. The method of claim 1, wherein the enrichment of at least one of the target products is controlled by the substrate feed of the anaerobic fermentation process.

6. The method of claim 1, wherein the enrichment of at least one of the target products is controlled by limiting at least one nutrient in the anaerobic fermentation process.

7. The method of claim 1, wherein the organic target product is obtained following a solid-liquid separation of the fermentation medium.

8. The method of claim 1, wherein the anaerobic fermentation process is carried out in multiple stages.

* * * * *